United States Patent [19]

Burnie

[11] Patent Number: 6,039,959
[45] Date of Patent: *Mar. 21, 2000

[54] TREATMENT AND DIAGNOSIS OF INFECTIONS DUE TO HELICOBACTER PYLORI

[75] Inventor: James Peter Burnie, Alderley Edge, United Kingdom

[73] Assignee: NeuTec Pharma plc, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 09/091,001
[22] PCT Filed: Nov. 27, 1996
[86] PCT No.: PCT/GB96/02907
  § 371 Date: Jun. 8, 1998
  § 102(e) Date: Jun. 8, 1998
[87] PCT Pub. No.: WO97/21103
  PCT Pub. Date: Jun. 12, 1997

[30] Foreign Application Priority Data

Dec. 6, 1995 [GB] United Kingdom .................. 9524934

[51] Int. Cl.[7] .................................................. A61K 39/02
[52] U.S. Cl. ...................... 424/234.1; 435/7.1; 435/7.32; 424/199.1; 424/217.1
[58] Field of Search ............................... 424/234.1, 94.6, 424/199.1, 217.1; 435/6, 7.21, 7.32, 7.93, 7.92, 320.1; 514/41, 234.5, 925, 926, 927

[56] References Cited

U.S. PATENT DOCUMENTS 5,837,240 11/1998 Lee et al. ................................ 424/94.6
5,843,460 12/1998 Labigne et al. ...................... 424/234.1

FOREIGN PATENT DOCUMENTS

93/20843 of 1993 WIPO .
93 07273 4/1993 WIPO .
94 06474 3/1994 WIPO .
94/09823 5/1994 WIPO .
95/22987 8/1995 WIPO .

OTHER PUBLICATIONS

Burnie and Al–Dughaym, Journal of Immunological Methods, vol. 194(1), pp. 85–94 (abstract), 1996.
Lee et al, Nov. 3–6, OraVax Inc, poster #13, Amelia Island, Florida, Helicobacter pylori Basic mechanisms to clinical cure (conference)., 1993.
Davin, et al., Proceeding of the DDW, American Gastroenterology Association, May 16–19, vol. 104(4), 1213, p. A–304, 1993.
Rappuoli et al, European Journal of Gastroenterology and Hepatology, vol. 5(Suppl 2), pp. S76–S78, 1993.
Thomas, Acta Gastro–Enterologica Belgica, Suppl., p. 54, 1993.
Czinn et al, vol. 11(6), pp. 637–642, 1993.
Blanchard et al, Acta Gastro Enterologica Belgica, Suppl, p. 53, 1993.
Ferrero et al, Gastroenterology, vol. 104(4), Apr., pp. A699, 1993.
Blaser, MJ, Trends in Microbiology, vol. 1(7), Oct., pp. 255–260, 1993.
Hu et al, Infection and Immunity, Jun. 1993, vol. 61(6), pp. 2563–2569, Jun. 1993.
Goodwin, C. Steward, Helicobacter pylori: Biology and Clinical Practice, Chapter 25, pp. 431–445, CRC Press, 1993.
Covacci et al, Immunobiol. Res. Inst. Sienna, Via Fiorentina 1, 53100 Sienna, ltl, vol. 0(0), pp. 43–50, 1994.
Li–Tai–Hu et al: "Purification of Recombinant ti Helicobacter pyloritI Urease Apoenzyme Encoded by ureA and ureB", Infection and Immunity, Jul. 1992, vol. 60, No. 7, pp 2657–2666, XP000670121.
Burnie et al: "The application of epitope mapping in the development of a new serological test for *Helicobacter pylori* infection", Journal of Immunological Methods, vol. 194, Jul. 17, 1996, pp 85–94, XP000670122.

*Primary Examiner*—James C. Housel
*Assistant Examiner*—Ginny Allen Portner
*Attorney, Agent, or Firm*—Pillsbury Madison & Sutro

[57] ABSTRACT

The present invention provides agents for the detection of urease from *H. pylori*, and agents and epitopes for use in the treatment or diagnosis of infection due to *H. pylori*, as well as diagnostic tests and kits therefor and the use of the agents and epitopes in the manufacture of medicaments.

7 Claims, 2 Drawing Sheets

TREATMENT AND DIAGNOSIS OF INFECTIONS DUE TO HELICOBACTER PYLORI

This application is a national phase of international application PCT/GB96/02907 filed Nov. 27, 1996 which designated the U.S.

The present invention concerns the prophylaxis, treatment and diagnosis of infections caused by *Helicobacter pylori*, together with methods for same.

*Helicobacter pylori* has recently been described as a cause of gastric ulcers, duodenal ulcers, gastric adenocarcinomas and atrophic gastritis (Lee, A. et al., 1993, Infect. Immun., 61: 1601–1610). Problems associated with it clinically are:

1. It is difficult to diagnose without an invasive biopsy, which has led to numerous attempts at a serological test, but there is no consensus of opinion as to which of these is best (Weiss, J. et al., 1994, J. Clin. Microbiol., 32: 1663–1668).

2. It is difficult to treat with conventional anti microbial chemotherapy (Czinn, S. J. et al., 1991, Infect. Immun., 39: 2359–2363) which has on that account been combined with anti-ulcer drugs such as Bismuth (Peterson, W. L., 1991, New England J. Med., 34: 1043–1048). The ulcers tend to recur, however.

It has been shown that antibody against urease (a key antigen) is a marker of infection (Nagata et al., 1992, Infect. Immun., 60: 4826–4831) and that one can vaccinate animals with urease and gain some protection (Lee, A. et al., supra. and Blanchard. T. G. et al., 1995, Infect. Immun., 63: 1394–1399).

Although the urease gene of *H. pylori* has been isolated and sequenced (Weiss. J. et al.. supra) and the protein encoded by the gene has also been sequenced key epitopes have not hitherto been identified.

The present invention provides agents for the detection of urease from *H. pylori*, and agents and epitopes for use in the treatment or diagnosis of infection due to *H. pylori*, as well as diagnostic tests and kits therefor and the use of the agents and epitopes in the manufacture of medicaments.

According to the present invention there is provided the use of an agent which binds specifically to an epitope selected from the group of LTPKELD (SEQ ID NO: 3) from ureA, and FISP (SEQ ID NO: 6), PTAF (SEQ ID NO: 13), EVGKVA (SEQ ID NO: 11) and SIP from ureB in a method of detection of urease from *H. pylori*, or a method of treatment or diagnosis of infection due to *H. pylori*.

Reference to epitopes is also reference to analogues thereof—to molecules which display the same epitope. Such molecules may, for example, be mimotopes (Geysen, H. M. et al., 1987, Journal of Immunological Methods, 102: 259–274) of the epitopes.

The agent may inhibit the (catalytic) activity of urease.

The agent may comprise an antibody or an antigen binding fragment thereof.

The antibody may be a whole antibody or an antigen binding fragment thereof and may in general belong to any immunoglobulin class. Thus, for example, it may be an immunoglobulin M antibody or an immunoglobulin G antibody. The antibody or fragment may be of animal, for example, mammalian origin and may be for example of murine, rat, sheep or human origin. It may be a natural antibody or a fragment thereof, or, if desired, a recombinant antibody fragment, i.e., an antibody or antibody fragment which has been produced using recombinant DNA techniques.

Particular recombinant antibodies or antibody fragments include, (1) those having an antigen binding site at least part of which is derived from a different antibody, for example those in which the hypervariable or complementarity determining regions of one antibody have been grafted into the variable framework regions of a second, different antibody (as described in, for example, European Patent Specification No 239400); (2) recombinant antibodies or fragments wherein non-Fv sequences have been substituted by non-Fv sequences from other, different antibodies (as described in, for example, European Patent Specification Nos 171469, 173494 and 194276); or (3) recombinant antibodies or fragments possessing substantially the structure of a natural immunoglobulin but wherein the hinge region has a different number of cysteine residues from that found in the natural immunoglobulin but wherein one or more cysteine residues in a surface pocket of the recombinant antibody or fragment is in the place of another amino acid residue present in the natural immunoglobulin (as described in, for example, International Patent Application Nos PCT/GB88/00730 and PCT/GB88/00729).

The antibody or antibody fragment may be of polyclonal or monoclonal origin. It may be specific for at least one epitope.

Antigen binding antibody fragments include, for example, fragments derived by proteolytic cleavage of a whole antibody, such as F(ab')2,Fab' or Fab fragments, or fragments obtained by recombinant DNA techniques, for example Fv fragments (as described, for example, in International Patent Application No PCT/GB88/0747).

The antibodies according to the invention may be prepared using well-known immunological techniques employing the protein expressed during infection as antigen. Thus, for example, any suitable host may be injected with the protein and the serum collected to yield the desired polyclonal antibody after appropriate purification and/or concentration (for example by affinity chromatography using the immobilised protein as the affinity medium). Alternatively splenocytes or lymphocytes may be recovered from the protein-injected host and immortalised using for example the method of Kohler et al. (1976, Eur. J. Immunol., 6: 511), the resulting cells being segregated to obtain a single genetic line producing monoclonal antibodies. Antibody fragments may be produced using conventional techniques, for example, by enzymatic digestion with pepsin or papain. Where it is desired to produce recombinant antibodies according to the invention these may be produced using, for example, the methods described in European Patent Specification Nos 171469, 173494, 194276 and 239400.

Antibodies according to the invention may be labelled with a detectable label or may be conjugated with an effector molecule, for example a drug e.g. an antibacterial agent or a toxin or an enzyme, using conventional procedures and the invention extends to such labelled antibodies or antibody conjugates.

According to the present invention there is also provided a diagnostic test for urease from *H. pylori* infection comprising the steps of:

i) reacting a sample to be tested with at least one agent according to the present invention;

ii) detecting a binding reaction; and iii) correlating detection of the binding reaction with the presence of urease from *H. pylori*.

The test may be for *H. pylori* infection, the sample being from a patient. Such diagnostic tests essentially determine whether the epitopes, and therefore the urease protein are present in a host organism. The test may be generally effected by contacting body fluid from the host with an agent according to the present invention and detecting any complexed material.

Hence when the agent comprises an antibody, a diagnostic test method for *H. pylori* infection may comprises the steps of:

i) reacting a sample of patient serum with at least one antibody according to the present invention;
ii) detecting a binding reaction; and
iii) correlating detection of the binding reaction with the infection by *H. pylori*.

The diagnostic test may comprise the use of at least one agent which binds specifically to ureA and at least one agent which binds specifically to ureB.

Appropriate types of diagnostic test are well known and may include indirect ELISA, radioimmunoassays and latex agglutination assays.

Also provided according to the present invention is a kit for performing a diagnostic test according to the present invention.

Also provided according to the present invention is the use of an agent according to the present invention in the manufacture of a medicament for treating infection due to *H. pylori*. Treatment may of course be therapeutic and/or prophylactic.

When used therapeutically, the agents of the present invention may be used in conjunction with pharmaceutically acceptable carriers, diluents and excipients (see for example Remington's Pharmaceutical Sciences and U.S. Pharmacopoeia (1984) Mack Publishing Company, Easton, Pa.).

In another use, the agents according to the present invention may be employed, using conventional techniques, for screening to obtain activity-inhibiting agents for use in the treatment of *Helicobacter pylori* infections.

According to the present invention there is also provided a method of detection of urease from *H. pylori*, or of treatment or diagnosis of infection due to *H. pylori* comprising the use of an agent which binds specifically to an epitope selected from the group of LTPKELD (SEQ ID NO: 3) from ureA, and FISP (SEQ ID NO: 6), PTAF (SEQ ID NO: 13), EVGKVA (SEQ ID NO: 11) and SIP from ureB.

According to a second aspect of the present invention there is provided the use of an epitope selected from the group of LTPKELD (SEQ ID NO: 3) from ureA, and FISP (SEQ ID NO: 6), PTAF (SEQ ID NO: 13), EVGKVA (SEQ ID NO: 11) and SIP from ureB in a method of detection of urease from *H. pylori*, or a method of treatment or diagnosis of infection due to *H. pylori*.

The epitopes may be used as immunogens or vaccines, and may be used in conjunction with an adjuvant.

According to the present invention there is also provided a diagnostic test for *H. pylori* infection comprising the steps of:

i) reacting serum from a patient with at least one epitope according to the present invention;
ii) detecting an antibody-antigen binding reaction; and
iii) correlating detection of the antibody-antigen binding reaction with infection by *H. pylori*.

The patient serum may for example comprise the IgM or IgA fraction of patient serum.

The epitopes used in the test may comprise at least one epitope from ureA and at least one epitope from ureB.

The diagnostic test may be an ELISA test, radioimmunoassay or latex agglutination assay.

Also provided according to the present invention is a kit for performing a diagnostic test according to the present invention.

Also provided according to the present invention is the use of an epitope according to the present invention in the manufacture of a medicament for treating infection due to *H. pylori*.

When used therapeutically, the epitopes of the present invention may be used in conjunction with pharmaceutically acceptable carriers, diluents and excipients.

In another use, the epitopes according to the present invention may be employed, using conventional techniques, for screening to obtain activity-inhibiting agents for use in the treatment of *Helicobacter pylori* infections.

According tot he present invention there is also provided a method of detection of urease from *H. pylori*, or of treatment or diagnosis of infection due to *H. pylori* comprising the use of an epitope selected from the group of LTPKELD (SEQ ID NO: 3) from ureA, and FISP (SEQ ID NO: 6), PTAF (SEQ ID NO: 13), EVGKVA (SEQ ID NO: 11) and SIP from ureB.

The contents of each of the references discussed herein, including the references cited therein, are herein incorporated by reference in their entirety.

BRIEF DESCRIPTION OF THE DRAWINGS

The invention will be further apparent from the following description, and from the diagrams of which

EXPERIMENTAL

Immunoblotting

Antigen Preparation

Figure 1:
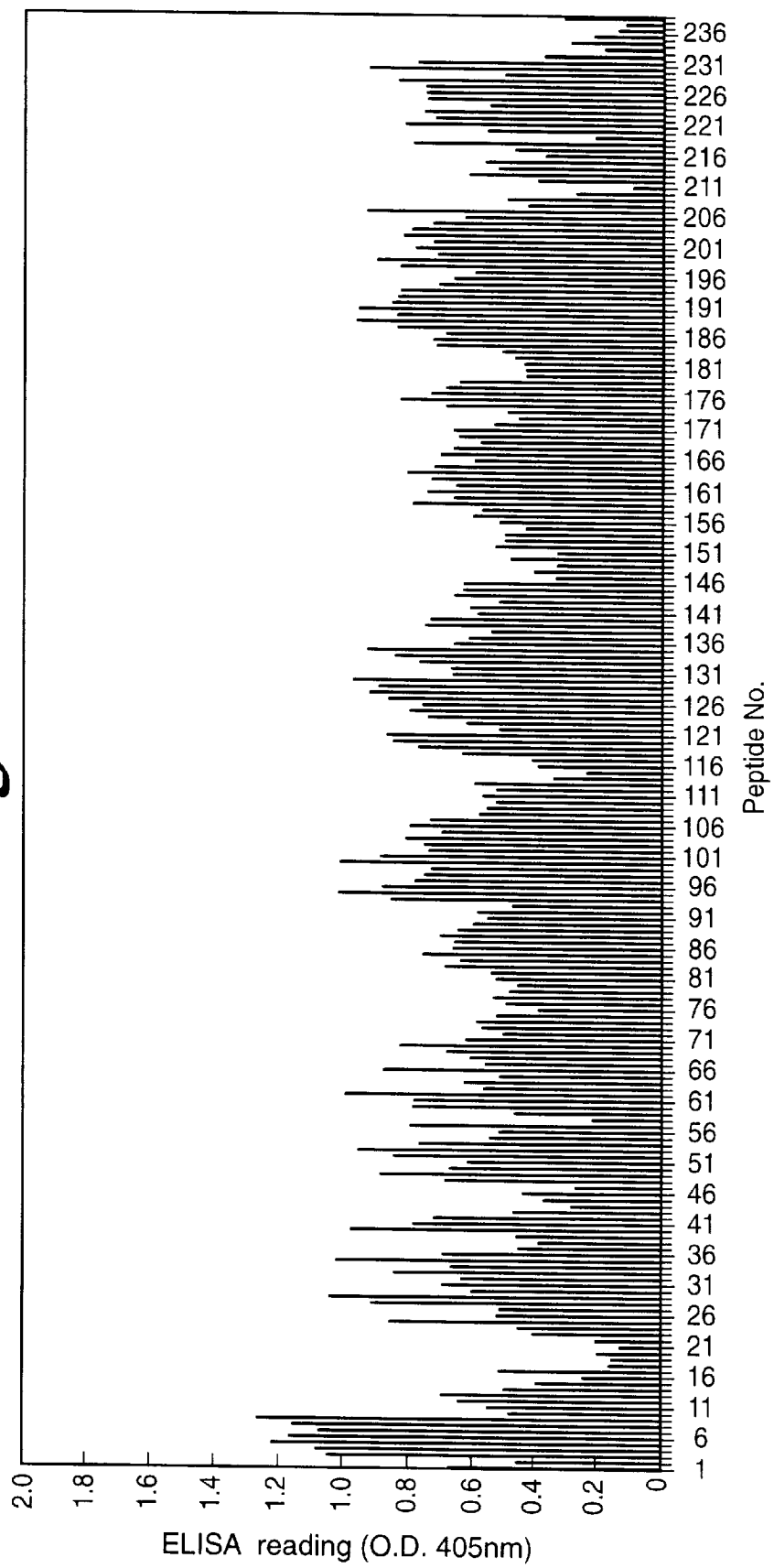
FIG. 1 shows the net ELISA readings of ureA, illustrating the only epitope (3–9) above the cut off point using 2SD. Cut off point=mean+2SD=1.034.

*H. pylori* strain NCTC 11637 was grown on Chocolate agar (Oxoid) for 3–4 days at 37° C. in a microaerophilic atmosphere. The cells were harvested and washed three times in distilled water. They were centrifuged at 4000 g for 10 minutes and the supernatant discarded. The sample was crushed three times in an Xpress (LKB, Bromma, Sweden) at a pressure of 200 mPa at −20° C. The disintegrated cells were centrifuged at 12,000 for 30 minutes at 4° C. The supernatant was stored at −20° C.

Sera

Group 1 Sera from patients who had *H. pylori* confirmed by biopsy and culture, a positive urease test on the biopsy and antibody against either the 31 or 62 Kda antigen of *H. pylori* on immunoblot.

Group 2 Sera from patients who were negative on biopsy and culture with a negative urease test on the biopsy.

SDS-PAGE and Immunoblotting

Immunoblots were prepared as described in detail elsewhere (Burnie, J. P. et al., 1988, J. Med. Microbiol., 27: 153–159). Briefly, 10 µl of *H. pylori* antigen was boiled for 5 minutes in 25 µl of SDS (sodium dodecyl sulphate) 2.6%, 2 mercaptoethanol 1.3% bromophenol blue 0.2% in 0.05 M Tris hydrochloride pH 6.8 and 15 µl of sterile distilled water and loaded onto a 10% polyacrylamide gel. This was run for 4 hours in a discontinuous buffer system. It was transferred on to a nitrocellulose membrane in an LKB Transblotter (LKB Bromma, Sweden).

The buffer contained methanol 20%, 25 mM Tris and 192 mM glycine at pH 8.3 and transfer was allowed to proceed at 25° C. for 45 minutes. The nitrocellulose paper was blocked in bovine serum albumin 3% in buffered saline (sodium chloride 0.9% and 10 mM Tris, pH 7.4) at 4° C. overnight. The nitrocellulose was then incubated at 25° C. for 2 hours with the serum from the patients diluted 1 in 10 in buffered saline containing bovine serum albumin 3% and Tween 20 0.05%. After washing five times+ for 30 minutes in saline 0.5% and Tween 20 0.05%, nitrocellulose strips were incubated for 1 hour at 25° C. with alkaline phosphatase-conjugated goat anti-human IgG, diluted 1 in 1000 in bovine serum albumin 3% in buffered saline. After washing again, as above, the membranes were incubated for 5–15 minutes at 25° C. with 100 ml of buffer (100 mM Tris-HCl, pH 9.5, 100 mM NaCl, 5 mM $MgCl_2$) containing a mixture of 660 μl of Nitro blue tetrazolium (NBT 50 mg/ml in N,N-dimethyl formamide 70%) and 330 μl of 5-bromo-4-chloro-3 inosolyl phosphate (BCIP 50 mg/ml in N,N-dimethyl formamide 70%). The reaction was stopped by washing in water. Immunoblots where the antibody response by reflectance densitometry (Chromoscan 3; Joyce Loebl) was greater than 50 mm were counted as positive.

Epitope Mapping

A series of overlapping nonapeptides covering the derived amino acid sequence of ureA and ureB (Clayton, C. et al., 1989, Nucl. Acid Res., 18:362) were synthesized with an epitope scanning kit (Cambridge Research Biochemicals, Cambridge, United Kingdom) manufacturers instructions were followed throughout. The reactivities of pin coupled synthetic peptides with the antisera from each patient (1:200 dilution) were determined for IgG by ELISA. Data were expressed at A405 after 30 minutes of incubation. Sera were examined from cases 1–10 (Group 1) and cases 1–5 (Group 2).

Indirect ELISA Test

Two of the epitopes defined by epitope mapping were synthesised as peptides. Peptide 1 (LTPKELDKLM LHYAG) (SEQ ID NO: 1) was from ureA and peptide 2 (VGSVEVGKVADLVLW) (SEQ ID NO: 2) was from ureB. Each peptide was dissolved in 50 mm phosphate buffered saline pH 7.0 at 10 μg/ml. 100 μl of the diluted peptide was added to each well of an ELISA plate and incubated overnight at 4° C. The plate was washed in PBS Tween 20 (0.05%) for 10 minutes, four times. Each serum was diluted 1 in 200 in super cocktail (ovalbumin 10 g/l, bovine serum albumen 10 g/l in PBS pH 7.2) and 100 μl was applied to three wells. These were incubated for 2 hours at 37° C. Washing was repeated and a 100 μl of the secondary antibody (horseradish peroxidase conjugated IgM or IgG (Sigma) at the correct working dilution) was added to each well. This was incubated at 37° C. for one hour. After washing, 150 μl of ABTS (amino-di-3-ethyl benzthiazole-6-sulphonate (Sigma) at 0.5 mg/ml in pH 4.0 citrate buffer with 0.03% hydrogen peroxide was added. Data was expressed as an optical density measured at A 405 after 30 minutes.

Results

Immun blotting the sera from Group 1 demonstrated that all of them had IgG against either or both the 31 or 62 Kda bands. In Group 2, one patient had antibody against the 31 Kda band and four against the band at 62 Kda. On the basis of this and the results of the routine tests, 10 sera (Patients 1–10, Table 1) were selected as positive by all criteria and 5 sera were negative by all criteria (Patients 1–5, Table 2).

Figure 2:
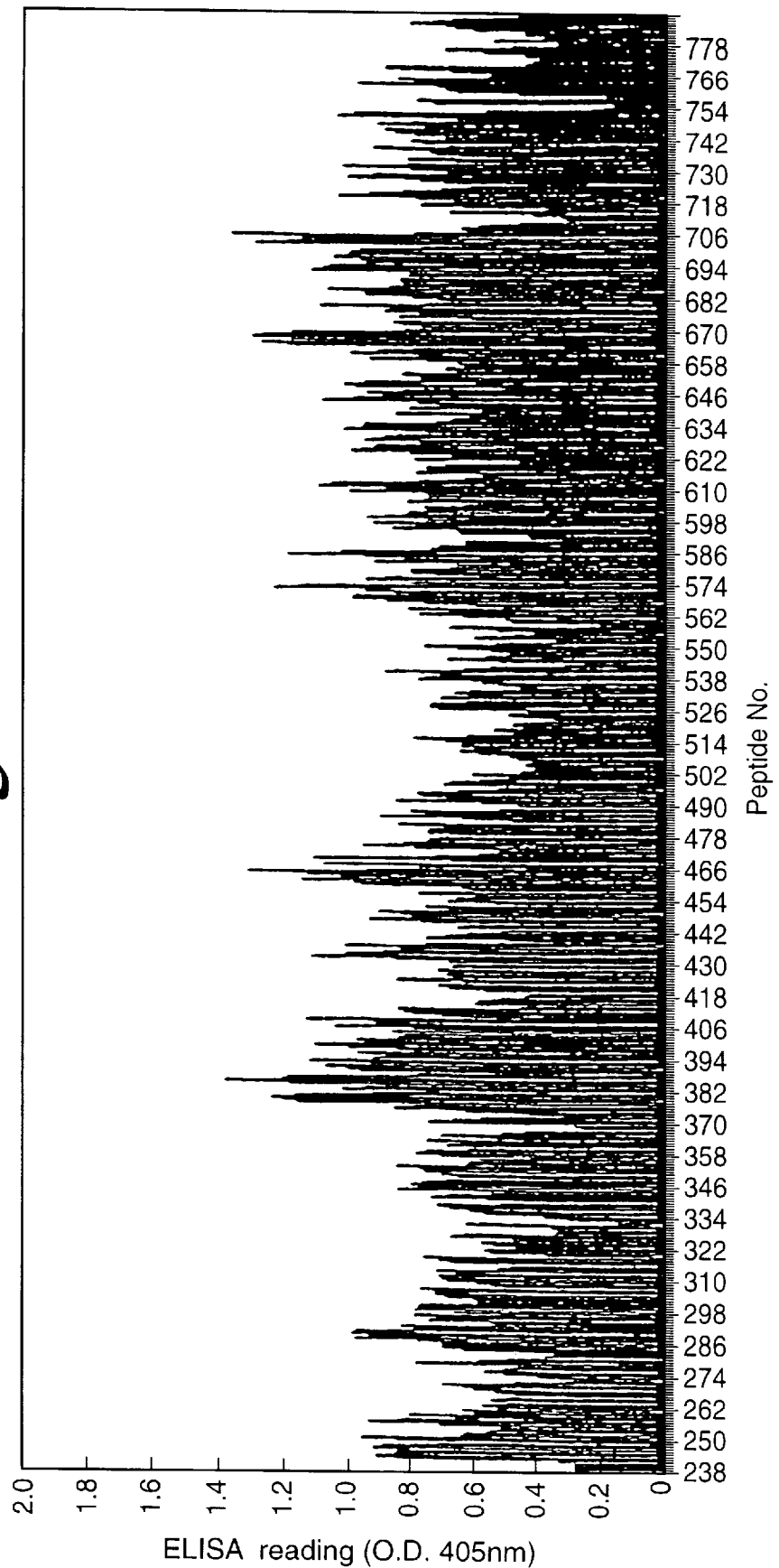
FIG. 2 shows the net ELISA reading of ureB of the urease protein after subtracting the average reading of control patients from positive patients. Cut off point=mean+2SD=1.133

When these were epitope scanned against ureA and ureB, the ELISA reading varied from 0.240 to 0.527 for the negative sera and from 0.491 to 2.654 for the positive sera. A net ELISA reading for each well was calculated by subtracting the average reading of all negative sera from the average reading of all the positive sera. This net ELISA reading represented any area of the protein where there was a clear differential between positive and control (FIGS. 1 and 2).

A cut off point was calculated for each subunit. This was defined as a mean plus one standard deviation of all the values of the net ELISA reading after subtracting the value for the negative patients for the ureA this was 0.830 and for ureB this was 0.929. Epitopes were further defined as being at least three and at most nine amino acids in length. The ureA had four epitopes and the ureB had 11 epitopes (Table 3). When the calculation was repeated with a cut off point of mean plus two standard deviations, epitope 1 (ureA) and epitopes 5, 6, 12 and 15 (ureB) still remained.

Peptide 1 was synthesised to represent epitope 1 and peptide 2 to represent epitope 12. These were evaluated in an indirect ELISA with the original sera as well as further cases (Tables 1 and 2). Assuming that Group 1 represented active *H. pylori* infection and Group 2 control patients and that an appropriate optical density cut off was 0.6 then the detection of IgM against either peptide 1 or peptide 2 had high specificity but low sensitivity (Table 3). IgG occurred more frequently in both negative and positive patients. The most efficient test (09.6%) was the detection of IgM against either or both peptides.

TABLE 1

Details of the Group 1 patients

| Patient No. | Clinical History | Immunoblotting 31 Kda | Immunoblotting 62 Kda | ELISA Optical Density Peptide 1 IgM | Peptide 1 IgG | Peptide 2 IgM | Peptide 2 IgG |
|---|---|---|---|---|---|---|---|
| 1 | Non ulcer dyspepsia | − | + | 1.811 | 0.466 | 1.572 | 0.942 |
| 2 | Non ulcer dyspepsia | − | + | 0.426 | 0.455 | 0.412 | 0.795 |
| 3 | Active gastric ulcer | − | + | 0.315 | 0.443 | 0.376 | 0.876 |
| 4 | Non ulcer dyspepsia | + | + | 0.428 | 0.716 | 0.580 | 1.081 |
| 5 | Non ulcer dyspepsia | + | + | 0.315 | 0.443 | 0.815 | 1.143 |
| 6 | Oesophagitis | − | + | 1.019 | 0.481 | 0.849 | 1.245 |
| 7 | Duodenal ulcer | − | + | 0.629 | 2.218 | 0.584 | 0.888 |
| 8 | Post duodenal ulcer | − | + | 0.271 | 0.565 | 0.545 | 0.363 |
| 9 | Gastric ulcer | + | + | 0.581 | 0.699 | 0.466 | 0.576 |
| 10 | Non ulcer dyspepsia | + | + | 0.572 | 1.442 | 0.749 | 1.515 |
| 11 | Duodenal ulcer | − | + | 0.428 | 1.061 | 0.608 | 0.334 |
| 12 | Duodenal ulcer | + | + | 0.379 | 0.553 | 0.426 | 0.761 |
| 13 | Non ulcer dyspepsia | + | + | 0.264 | 0.575 | 0.311 | 0.507 |
| 14 | Active duodenal ulcer | + | − | 0.329 | 0.649 | 0.369 | 2.583 |
| 15 | Non ulcer dyspepsia | − | + | 0.485 | 0.811 | 0.602 | 1.900 |
| 16 | Non ulcer dyspepsia | + | − | 0.278 | 0.985 | 0.284 | 0.534 |
| 17 | Oesophagitis | + | − | 0.697 | 0.354 | 0.524 | 0.332 |
| 18 | Active duodenal ulcer | − | + | 0.624 | 2.987 | 0.278 | 0.335 |
| 19 | Non ulcer dispepsia | + | + | 0.627 | 1.168 | 0.584 | 0.907 |

TABLE 2

Details of the Group 2 patients

| Patient No. | Clinical History | Immunoblotting 31 Kda | Immunoblotting 62 Kda | ELISA Optical Density Peptide 1 IgM | Peptide 1 IgG | Peptide 2 IgM | Peptide 2 IgG |
|---|---|---|---|---|---|---|---|
| 1 | Oesophagitis | − | − | 0.264 | 0.325 | 0.221 | 0.315 |
| 2 | Non ulcer dyspepsia | − | − | 0.520 | 0.453 | 0.472 | 0.482 |
| 3 | Healed duodenal ulcer | − | − | 0.299 | 0.453 | 0.284 | 0.463 |
| 4 | Non ulcer dyspepsia | − | − | 0.419 | 0.379 | 0.345 | 0.420 |
| 5 | Non ulcer dyspepsia | − | − | 0.271 | 1.233 | 0.213 | 0.446 |
| 6 | Screening anaemia | − | + | 0.766 | 0.676 | 0.490 | 0625 |
| 7 | Duodenal ulcer post | − | + | 0.295 | 1.328 | 0.265 | 1.432 |

TABLE 2-continued

Details of the Group 2 patients

| Pa-tient No. | Clinical History | Immuno-blotting 31 Kda | Immuno-blotting 62 Kda | ELISA Optical Density Peptide 1 IgM | ELISA Optical Density Peptide 1 IgG | ELISA Optical Density Peptide 2 IgM | ELISA Optical Density Peptide 2 IgG |
|---|---|---|---|---|---|---|---|
| | treatment | | | | | | |
| 8 | Non ulcer dyspepsia | − | + | 0.482 | 0.633 | 0.523 | 0.756 |
| 9 | Duodenal ulcer post treatment | − | − | 0.556 | 0.897 | 0.394 | 0.326 |
| 10 | Non ulcer dyspepsia | − | − | 0.584 | 0.627 | 0.477 | 0.338 |
| 11 | Erosive gastritis | + | − | 0.454 | 0.711 | 0.519 | 1.791 |
| 12 | Duodenal ulcer post treatment | − | − | 0.434 | 0.900 | 0.271 | 0.562 |
| 13 | Non ulcer dyspepsia | − | + | 0.354 | 0.416 | 0.298 | 0.509 |
| 14 | Non ulcer dyspepsia | − | − | 0.361 | 0.650 | 0.263 | 0.409 |

TABLE 3

Details of the sensitivity, specificity and efficiency of the indirect ELISA

| | Peptide 1 IgM | Peptide 1 IgG | Peptide 2 IgM | Peptide 2 IgG | Peptide 1 and/or 2 IgM | Peptide 1 and/or 2 IgG |
|---|---|---|---|---|---|---|
| True negative | 13 | 5 | 14 | 10 | 13 | 5 |
| False negative | 13 | 9 | 13 | 7 | 9 | 3 |
| True positive | 6 | 10 | 6 | 12 | 10 | 16 |
| False positive | 1 | 9 | 0 | 4 | 1 | 9 |
| Sensitivity | 31.6% | 52.6% | 31.6% | 36.8% | 52.6% | 84.2% |
| Specificity | 92.8% | 35.7% | 100% | 71.4% | 92.8% | 35.7% |
| Efficiency | 57.5% | 45.4% | 60.6% | 66.6% | 69.6% | 63.6% |

TABLE 4

The total numbers of epitopes with their positions and sequences for both ureA and ureB due to 1 SD (standard deviation).

| Sub-units | Peptide No. | SEQ ID NO | AA positions | Amino Acid Sequences |
|---|---|---|---|---|
| ALPHA | 1 | 3 | 3–9 | LPTKELD |
| | 2 | — | 94–96 | VTV |
| | 3 | 4 | 127–130 | VSVK |
| | 4 | 5 | 188–194 | DIGGNRR |
| BETA | 5 | 6 | 377–380 | FISP |
| | 6 | 7 | 382–387 | QIPTAF |
| | 7 | — | 389–391 | SGV |
| | 8 | 8 | 398–401 | GTGP |
| | 9 | 9 | 460–466 | EDWGTTP |
| | 10 | — | 633–635 | GDN |
| | 11 | 10 | 644–651 | LSKYTINP |
| | 12 | 11 | 665–670 | EVGKVA |
| | 13 | — | 684–686 | PNM |
| | 14 | 12 | 693–701 | IALSQMGDA |
| | 15 | — | 704–706 | SIP |

TABLE 5

The total numbers of epitopes with their positions and sequences for both ureA and ureB due to 2 SD (standard deviations).

| Sub-units | Peptide No. | SEQ ID NO | AA positions | Amino Acid Sequences |
|---|---|---|---|---|
| ALPHA | 1 | 3 | 3–9 | LTPKELD |
| BETA | 2 | 6 | 377–380 | FISP |
| | 3 | 13 | 384–387 | PTAF |
| | 4 | 11 | 665–670 | EVGKVA |
| | 5 | — | 704–706 | SIP |

I claim:

1. A method of treating *Helicobacter pylori* infection comprising providing epitope EVGKVA (SEQ ID NO:11), selecting an antibody to said epitope, and administering said antibody or a fragment thereof to an individual at risk from *H. pylori* infection.

2. A method of manufacturing a medicament for the treatment of infection due to *H. pylori* comprising selecting an antibody to epitope EVGKVA (SEQ ID NO:11) and combining said antibody or a fragment thereof with at least one pharmaceutically acceptable carrier or delivery vehicle.

3. An isolated and purified antibody specific for epitope EVGKVA (SEQ ID NO:11).

4. A composition comprising an isolated and purified antibody or fragment thereof specific for epitope EVGKVA (SEQ ID NO:11).

5. The composition of claim 4 wherein said antibody is a monoclonal antibody.

6. The composition of claim 4 wherein said fragment is a single chain Fv fragment.

7. A method of diagnosis of infection due to *H. pylori*, comprising obtaining a biological sample from an individual at risk from *H. pylori* infection, contacting said sample with epitope EVGKVA (SEQ ID NO:11), the presence of antibodies in said sample reactive with said epitope being indicative of infection.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
      (A) LENGTH: 15 amino acids
      (B) TYPE: amino acid
      (C) STRANDEDNESS:
      (D) TOPOLOGY: unknown (xi) SEQUENCE DESCRIPTION: SEQ ID NO: 1:

Leu Thr Pro Lys Glu Leu Asp Lys Leu Met Leu His Tyr Ala Gly
1          5                 10              15

(2) INFORMATION FOR SEQ ID NO: 2:

```
        (i) SEQUENCE CHARACTERISTICS:
            (A) LENGTH: 15 amino acids
            (B) TYPE: amino acid
            (C) STRANDEDNESS:
            (D) TOPOLOGY: unknown (xi) SEQUENCE DESCRIPTION: SEQ ID NO: 2:

Val Gly Ser Val Glu Val Gly Lys Val Ala Asp Leu Val Leu Trp
1               5                   10                  15

(2) INFORMATION FOR SEQ ID NO: 3:

(i) SEQUENCE CHARACTERISTICS:
            (A) LENGTH: 7 amino acids
            (B) TYPE: amino acid
            (C) STRANDEDNESS:
            (D) TOPOLOGY: unknown (xi) SEQUENCE DESCRIPTION: SEQ ID NO: 3:

Leu Thr Pro Lys Glu Leu Asp
1               5

(2) INFORMATION FOR SEQ ID NO: 4:

(i) SEQUENCE CHARACTERISTICS:
            (A) LENGTH: 4 amino acids
            (B) TYPE: amino acid
            (C) STRANDEDNESS:
            (D) TOPOLOGY: unknown (xi) SEQUENCE DESCRIPTION: SEQ ID NO: 4:

Val Ser Val Lys
1

(2) INFORMATION FOR SEQ ID NO: 5:

(i) SEQUENCE CHARACTERISTICS:
            (A) LENGTH: 7 amino acids
            (B) TYPE: amino acid
            (C) STRANDEDNESS:
            (D) TOPOLOGY: unknown (xi) SEQUENCE DESCRIPTION: SEQ ID NO: 5:

Asp Ile Gly Gly Asn Arg Arg
1               5

(2) INFORMATION FOR SEQ ID NO: 6:

(i) SEQUENCE CHARACTERISTICS:
            (A) LENGTH: 4 amino acids
            (B) TYPE: amino acid
            (C) STRANDEDNESS:
            (D) TOPOLOGY: unknown (xi) SEQUENCE DESCRIPTION: SEQ ID NO: 6:

Phe Ile Ser Pro
1

(2) INFORMATION FOR SEQ ID NO: 7:

(i) SEQUENCE CHARACTERISTICS:
            (A) LENGTH: 6 amino acids
            (B) TYPE: amino acid
            (C) STRANDEDNESS:
            (D) TOPOLOGY: unknown (xi) SEQUENCE DESCRIPTION: SEQ ID NO: 7:
```

```
Gln Ile Pro Thr Ala Phe
1               5

(2) INFORMATION FOR SEQ ID NO: 8:

(i) SEQUENCE CHARACTERISTICS:
        (A) LENGTH: 4 amino acids
        (B) TYPE: amino acid
        (C) STRANDEDNESS:
        (D) TOPOLOGY: unknown (xi) SEQUENCE DESCRIPTION: SEQ ID NO: 8:

Gly Thr Gly Pro
1

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS:
        (D) TOPOLOGY: unknown (xi) SEQUENCE DESCRIPTION: SEQ ID NO: 9:

Glu Asp Trp Gly Thr Thr Pro
1               5

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS:
        (D) TOPOLOGY: unknown (xi) SEQUENCE DESCRIPTION: SEQ ID NO: 10:

Leu Ser Lys Tyr Thr Ile Asn Pro
1               5

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS:
        (D) TOPOLOGY: unknown (xi) SEQUENCE DESCRIPTION: SEQ ID NO: 11:

Glu Val Gly Lys Val Ala
1               5

(2) INFORMATION FOR SEQ ID NO: 12:

(i) SEQUENCE CHARACTERISTICS:
        (A) LENGTH: 9 amino acids
        (B) TYPE: amino acid
        (C) STRANDEDNESS:
        (D) TOPOLOGY: unknown (xi) SEQUENCE DESCRIPTION: SEQ ID NO: 12:

Ile Ala Leu Ser Gln Met Gly Asp Ala
1               5

(2) INFORMATION FOR SEQ ID NO: 13:

(i) SEQUENCE CHARACTERISTICS:
        (A) LENGTH: 4 amino acids
        (B) TYPE: amino acid
```

-continued

```
        (C) STRANDEDNESS:
        (D) TOPOLOGY: unknown (xi) SEQUENCE DESCRIPTION: SEQ ID NO: 13:

Pro Thr Ala Phe
```